United States Patent [19]

Graham

[11] Patent Number: 4,502,163
[45] Date of Patent: Mar. 5, 1985

[54] HAPTIC FOR INTRAOCULAR LENS

[75] Inventor: William M. Graham, Burton, Wash.

[73] Assignee: Cooper Vision, Inc., Palo Alto, Calif.

[21] Appl. No.: 539,997

[22] Filed: Oct. 7, 1983

[51] Int. Cl.³ .............................. A61F 1/16; A61F 1/24
[52] U.S. Cl. .......................................................... 3/13
[58] Field of Search ........................................... 3/13, 1

[56] References Cited

U.S. PATENT DOCUMENTS

| | | | |
|---|---|---|---|
| 3,971,073 | 7/1976 | Richards et al. | 3/13 |
| 3,975,779 | 8/1976 | Richards et al. | 3/13 |
| 3,996,626 | 12/1976 | Richards et al. | 3/13 |
| 4,012,823 | 3/1977 | Richards | 3/13 |
| 4,014,049 | 3/1977 | Richards et al. | 3/13 |
| 4,025,965 | 5/1977 | Siegmund | 3/13 |
| 4,143,427 | 3/1979 | Anis | 3/13 |
| 4,166,293 | 9/1979 | Anis | 3/13 |
| 4,174,543 | 11/1979 | Kelman | 3/13 |
| 4,254,511 | 3/1981 | Chase et al. | 3/13 |
| 4,257,130 | 3/1981 | Bayers | 3/13 |
| 4,268,921 | 5/1981 | Kelman | 3/13 |
| 4,285,072 | 8/1981 | Morcher et al. | 3/13 |
| 4,304,012 | 12/1981 | Richard | 3/13 |
| 4,316,293 | 2/1982 | Bayers | 3/13 |
| 4,328,595 | 5/1982 | Sheets | 3/13 |
| 4,418,431 | 12/1983 | Feaster | 3/13 |
| 4,437,194 | 3/1984 | Hahs | 3/13 |

OTHER PUBLICATIONS

American Medical Optics, Model PC-80, Posterior Chamber (Knolle) Intraocular Lenses (advertisement) American Medical Optics, American Hospital Supply Corp., 1402 East Alton Ave., Irvine, CA 92714 (4 pages) Sep. 1982.

Primary Examiner—Ronald L. Frinks
Attorney, Agent, or Firm—Christensen, O'Connor, Johnson & Kindness

[57] ABSTRACT

An intraocular lens for placement in the anterior or posterior chamber of the eye after extracapsular surgery has one or more haptics having an asymmetrical cross section. The haptic is formed in a continuous loop. Preferably both ends of the haptic are joined to the optic at a single location. A preferred cross-sectional shape is a major segment of a circle.

13 Claims, 4 Drawing Figures

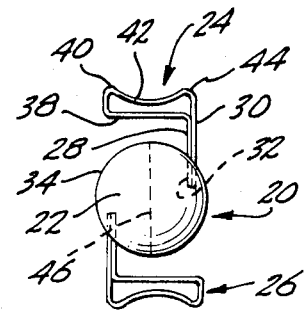
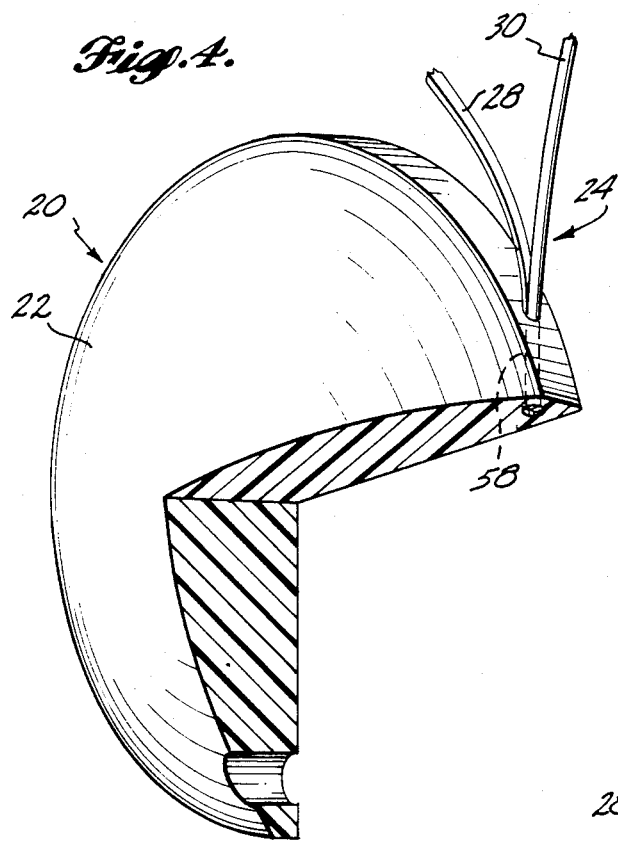
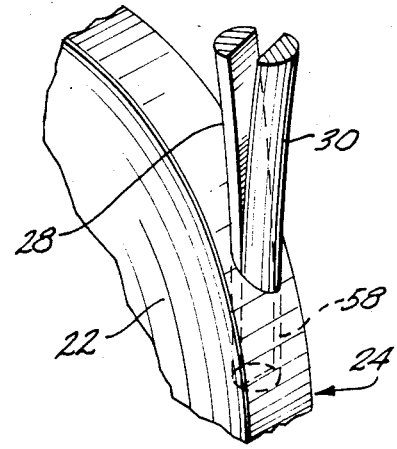
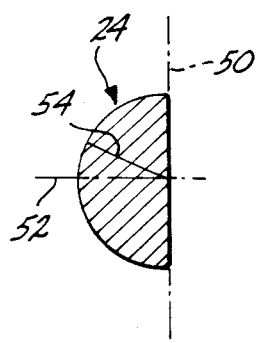
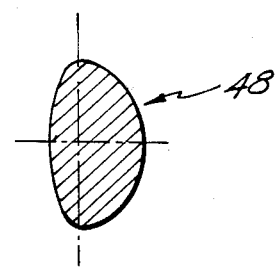

HAPTIC FOR INTRAOCULAR LENS

BACKGROUND OF THE INVENTION

The present invention relates to intraocular lenses, and more particularly, to improved haptics therefor.

Intraocular lenses are employed as replacements for the crystalline lens after either extracapsular or intracapsular surgery for the removal of a cataract. Intraocular lenses are generally of two types, those that are placed in the anterior chamber, i.e., between the iris and cornea, and those that are placed in the posterior chamber, i.e., behind the iris. Both types of lenses are conventionally employed with a choice between an anterior and a posterior lens being partly dictated by requirements of the patient and partly dictated by the preferences of the physician inserting the lens.

Intraocular lenses normally consist of an optic with two or more haptics that extend generally radially from the optic and contain foot portions that normally seat in the scleral spur for an anterior lens and either in the ciliary sulcus or within the lens capsule for a posterior lens. The optic normally comprises a circular transparent optical lens. The haptic in most lenses is a flexible fiber or filament having one end affixed to the lens and having a second portion extending radially away from the lens to form the seating foot. Several haptic designs are currently in use, for example, a pair of U-shaped loops in which both ends of each loop are connected to the lens and, for example, J-shaped loops in which only one end of the loop is affixed to the lens.

When anterior lenses are employed, care must be taken when inserting the lens and seating the haptics in the scleral spur that the lens itself does not move forwardly so that it contacts the endothelial lining on the posterior side of the cornea. Contact with the endothelial layer is detrimental because destruction of too many endothelial cells will result in corneal decompensation and subsequent opacification of the cornea. One of the drawbacks of conventional anterior lens designs is that when the flexible haptics are compressed, the lens is thrust forwardly along the optical axis. This reaction of the optic to haptic compression causes the optic to move forwardly toward and possibly to contact the endothelial layer as the lens is being inserted. Moreover, once the lens is inserted, if the eye is distorted, for example, by an accidental blow, the haptics can be compressed, vaulting the optic forwardly into the endothelial layer. One solution to vaulting is the use of posterior lenses. However, there are still situations when use of an anterior lens is dictated or desired.

One suggested solution for eliminating vaulting in anterior chamber lens is contained in U.S. Pat. No. 4,316,293 to John H. Bayers. Bayers suggests the use of a haptic having a symmetrical cross section with a minor dimension and a major dimension, the major dimension being oriented generally parallel to the axis of the optic. According to Bayers, this haptic configuration will allow the haptic to flex only in the direction of the minor axis, i.e., generally in the direction perpendicular to the major axis of the haptic. Thus, according to Bayers, whether the haptics are compressed for insertion or by an accidental blow to the eye or for any other reason, the haptics will spread only outwardly from each other and in theory alleviate the vaulting problem.

It has been found, however, that with haptics having a cross section as suggested by Bayers, for example, and oval cross section, the optic still vaults, that is, moves along the optical axis as the haptics are compressed. Moreover, the legs of the Bayers' haptics, that is the portions of the haptics extending from the lens to the seating portions of the haptics tend to move laterally in the same direction, causing the optic to move sideways relative to the optic axis. At the same time, the haptic may twist, causing the lens to rotate about an axis generally perpendicular to the optical axis. All three of these tendencies, i.e., the vaulting, the sideward movement, and the twisting are undesirable not only during insertion, but also once the lens has been implanted.

SUMMARY OF THE INVENTION

The present invention provides a solution to the foregoing problems by employing a haptic cross section at least a portion of which is asymmetric about an axis oriented generally parallel to the optic axis. More specifically, the present invention provides an intraocular lens for placement in the eye comprising an optic and at least one haptic. The optic has an optical axis extending through the central portion thereof. A channel is provided in the optic that extends from the optic periphery into the optic. The asymmetrical cross section of the haptic has major and minor axes. The major axis is oriented generally parallel to the optical axis while the minor axis is oriented generally orthogonally to the major axis. The haptic has first and second ends, the first of which is inserted in the channel in the optic. From its first end, the haptic extends outwardly to form an eye contacting portion and, thereafter, extends inwardly toward the second end, which is juxtaposed the first end in the optic channel. Thus, a haptic constructed in accordance with the present invention provides a continuous loop, both ends of which can be mounted in a single hole. A preferred cross section comprises a planar geometric figure that approximates in shape a sector of a circle bounded by a diameter of a circle and a 180° arc of that circle, which will hereinafter be referred to as a 180° sector. The channel in the optic then can comprise a single bore that is easy to fabricate and that readily receives the juxtaposed ends of the haptic, which when juxtaposed form a cylindrical shape. A haptic constructed in accordance with the present invention, because of its asymmetrical nature and because it is formed into a continuous loop extending from a single channel, does not cause the optic to vault when the haptics are compressed. Moreover, the haptic does not allow the optic to move sideways or to twist as the haptic is compressed.

BRIEF DESCRIPTION OF THE DRAWINGS

A better understanding of the present invention can be derived by reading the ensuing specification in conjunction with the accompanying drawings wherein:

FIG. 1 is an elevation view of an intraocular lens having a haptic constructed in accordance with the present invention;

FIG. 2 is a cross-sectional view of the general shape of a haptic constructed in accordance with the present invention;

FIG. 3 is cross-sectional view of a preferred haptic constructed in accordance with the present invention;

FIG. 4 is an isometric view of the lens with a quarter segment broken away to illustrate the attachment to the optic of the two ends of a haptic constructed in accordance with the present invention to the optic; and FIG. 5 is an enlarged isometric view of the attachment of the haptic to the optic.

DETAILED DESCRIPTION OF THE INVENTION

Referring first to FIG. 1, an intraocular lens 20 constructed in accordance with the present invention includes an optic 22 and at least one haptic 24, and preferrably a second haptic 26 constructed in accordance with the present invention. Haptic 24 includes first and second leg portions 28 and 30, the ends of which are juxtaposed in a channel 32 formed in the optic 22. Both of the legs 28 and 30 extend outwardly from the periphery 34 of the optic 22 in an outward direction generally parallel to a tangent to the periphery of the optic. At a predetermined distance from the optic 22, leg 28 transitions in a smooth 90° arc into bridge 38. The bridge portion curves back on itself to form a first convex, eye contact portion 40. The convex portion reverses curvature to form a concave outer arch portion 42 spaced outwardly from the inner arch portion. The concave portion changes slope again to form a second convex contact portion 44 spaced from the first contact portion. The second contact portion curves downwardly to form a continuous extension of the second leg 30. In this manner, the haptic is formed from a continuous strand of material.

The second haptic 26, positioned on the opposite side of the optic from the first haptic 24, is constructed identically to the first haptic. The second haptic is joined to the optic 22 at a position 180° from location where legs 28 and 30 of haptic 24 are joined to the lens. Also, legs of the haptics 24 and 26 are parallel to each other and to a diameter 46 of the optic and are affixed to the optic at locations offset in a clockwise direction from opposite ends of the diameter 46.

Haptics constructed in accordance with the present invention can be made from a variety of materials including polymethylmethacrylate and polypropylene. These materials are sufficiently flexible and resilient to function as haptics and are relatively inert so that they are safe for implantation in the eye. Referring now to FIG. 2, a haptic 48 constructed in accordance with the present invention has a unique cross section that is asymmetrical about a major axis 50 and that is generally symmetrical with respect to a minor axis 52 that is oriented orthogonally to the major axis 50. The generalized cross section shown is generally oblate on the left side of the major axis 50 and is relatively prolate on the right side of the major axis 50, leaving a substantial portion of said haptic on the right side of the major axis. Thus, the filament from which the haptic 48 is made while generally being convex on both side of the major axis has substantially more surface area on the right side of the major axis than on the left side. This unique shape of the filament provides the haptic with its unique characteristics so that when compressed in a generally radial direction the optic will tend neither to vault nor to twist relative to the haptics, but instead will stay relatively stationary in the direction of the optical axis. It has been found that the height to thickness ratio (measured on the major and minor axes respectively) can vary from 1.7 to 2.3 and still display these desired characteristics.

Referring now to FIG. 3, a preferred cross section for constructing haptics in accordance with the present invention is illustrated. In. FIG. 3, the cross section of the haptic 24 may be shaped as a 180° sector of a circle having a radius 54. In this embodiment, the left side of the haptic in cross section is in essence coincident with the major axis. The 180° sector is therefore a preferred cross-sectional area for haptics constructed in accordance with the present invention as it retains its asymmetric shape about a major axis 50 while maximizing the surface area on the one side of the major axis 50 and minimizing it on the other side. It is also preferred that the cross-sectional shape only approximate a 180° sector since it is most desirable to smoothly round the sector where the arc joins the diameter of the sector, thus eliminating any sharp edges. This cross section also has other advantages as will be described in more detail.

Referring now to FIGS. 4 and 5, a preferred method of attachment of the haptic constructed in accordance with the present invention is illustrated. The ends of the two legs 28 and 30 of the haptic 24 are joined to the optic 22 by inserting them in a channel 58 formed in the optic 22. The channel 58 can be oriented generally parallel to a tangent to the periphery of the optic 22, which would position the channel to lie within a plane oriented orthogonally to the optical axis of the lens. Or, the channel can be canted slightly to such a plane so that the haptic extends rearwardly at a shallow angle from the optic.

Since the filaments forming the two legs 30 and 32 of the haptic 24 have the preferred cross section, i.e., a 180° sector, channel 58 can be cylindrical in shape. Channel 58 can be molded, bored or otherwise machined in the optic 22. A preferred method of forming the channel 58 is to bore it as one of the machining procedures on the lens. As better illustrated in FIG. 5, the ends of legs 28 and 30 are both inserted in juxtaposed relationship in the channel 58 so that the flat sides of the filaments contact each other. The diameter of the channel 58 is sized, of course, so that the two ends of the legs 30 and 32 fit snugly into the channel 58. Once the ends of the legs 30 and 32 are inserted and rotationally oriented to provide the proper haptic orientation relative to the optic, the legs can be joined to the optic by way of a number of conventional means such as adhesively or by ultrasonic welding.

This technique of mounting the haptic to the optic can also be employed using a haptic having a circular or other symmetrical cross-sectional shape, such as in connection with a posterior chamber lens where the vaulting problem is not as pronounced. For example, the ends of a haptic having a circular cross section can be formed into the desired asymmetrical shape. Forming of these ends into an asymmetrical shape such as an approximation of a 180° sector of a circle can be accomplished by subjecting the ends to heat and/or pressure in an appropriately shaped mold. Once both ends of a haptic have been so formed, they can be fitted into a single bore in a manner similar to a haptic entirely composed of a symmetrical cross section. Thus, in situations where advantage need not be taken of the nonvaulting characteristics of entirely asymmetrical haptic constructed in accordance with the present invention, the cost savings of using a round haptic combined with mounting of its ends in a single bore can still be enjoyed.

The present invention has been described in conjunction with the preferred embodiment and several alternates thereto. One of ordinary skill after reading the foregoing specification will be able to effect various changes, substitutions of equivalents and other alterations without departing from the broad concepts imparted herein. For example, one of ordinary skill will readily realize that asymmetrical cross-sectional shape of the haptics constructed in accordance with the present invention does not dictate that the ends of the haptic be joined to the optic at a single location. As an alternative to the juxtaposed fixational location, the ends of the haptic can be joined to the optic at spaced locations. While the haptic constructed in this manner will perform virtually identical to the haptics joined in a single juxtaposed location, the cost and effort in affixing the haptic to the optic is increased. Additionally, haptics constructed as disclosed can be employed with both anterior and posterior chamber lenses. It is therefore intended that the protection afforded by Letters Patent granted hereon be limited only by the definition contained in the appended claims and equivalents thereof.

The embodiments of the invention in which an exclusive property or privilege is being claimed are defined as follows:

1. An intraocular lens for placement in the eye comprising:
   an optic having an optical axis extending through the central portion thereof, said optic having a channel therein extending inwardly from the periphery thereof; and,
   at least one haptic, said haptic being flexible, at least a portion of said haptic having an asymmetrical cross section, said haptic in cross section having a major axis and a minor axis, said major axis being oriented generally parallel to said optical axis, said minor axis being oriented generally orthogonally to said major axis, said haptic having first and second ends, said first end being inserted in said channel, said haptic extending outwardly from said first end and the periphery of said optic to form an eye contacting portion and, thereafter, extending inwardly toward said periphery and said second end, said second end being juxtaposed said first end in said channel.

2. The lens of claim 1, wherein said channel is circular in cross section, and wherein the portion of the haptic having said asymmetrical cross section comprises said first and second ends.

3. The lens of claim 2 wherein said entire haptic has said asymmetrical cross section.

4. The lens of claim 2, wherein said optic is circularly shaped, the longitudinal axis of said channel being oriented substantially parallel to a tangent to the periphery of said optic.

5. The lens of claim 4, wherein the cross section of said haptic approximates a 180° sector of a circle.

6. The lens of claim 5, wherein the combined cross section of said first and second ends of said haptic when in juxtaposed relationship in said channel approximate a circle.

7. The lens of claim 1, wherein the surface of said haptic on a first side of said major axis is substantially greater than the surface on the second side of said major axis.

8. The lens of claim 7, wherein the surface of said first side is convex.

9. The lens of claim 1, wherein a substantial portion of the cross section of said haptic lies on one side of said major axis.

10. The lens of claim 9, wherein the surface of said haptic on said one side is convex relative to said major axis.

11. The lens of claim 10, wherein the surface of said haptic opposite said one side is substantially coincident with said major axis.

12. The lens of claim 11, wherein the cross section of said haptic is substantially a 180° sector of a circle.

13. The lens of claim 1 wherein at least that portion of the haptic lying between said first and second ends has said asymmetrical cross section.

* * * * *